United States Patent [19]

Surjaatmadja et al.

[11] Patent Number: 5,192,509
[45] Date of Patent: Mar. 9, 1993

[54] APPARATUS FOR AUTOMATIC TITRATION

[75] Inventors: Jim B. Surjaatmadja; Clyde L. Lee, both of Duncan, Okla.

[73] Assignee: Halliburton Company, Duncan, Okla.

[21] Appl. No.: 748,986

[22] Filed: Aug. 22, 1991

[51] Int. Cl.[5] .......................................... G01N 31/16
[52] U.S. Cl. ....................................... 422/75; 422/81; 422/82.05; 422/82.09; 436/51; 436/52; 436/163
[58] Field of Search ................... 422/75, 82.05, 82.09, 422/81, 76, 77; 436/51, 52, 163

[56] References Cited

U.S. PATENT DOCUMENTS

| | | | |
|---|---|---|---|
| 3,565,286 | 2/1971 | Latham | 422/81 X |
| 3,787,291 | 1/1974 | Deuringer et al. | 422/82.05 X |
| 4,749,552 | 6/1988 | Sakisako et al. | 422/75 |
| 4,930,898 | 6/1990 | Miller-Ihli | 422/65 X |
| 4,950,610 | 8/1990 | Tittle | 422/75 X |

Primary Examiner—Jill A. Johnston
Assistant Examiner—Maureen M. Wallenhorst
Attorney, Agent, or Firm—James R. Duzan; Robert M. Hessin

[57] ABSTRACT

An automatic titration device for use in either batch processing or a continuous processing mode to identify quantitative fluid properties. The device consists of a plurality of reservoirs each connected to a respective plurality of pumps. A central computer controls individual pump speeds and therefore the pump output mix through a delivery tube that delivers fluid mixture through an ultrasonic mixer to a mixing tube whereupon a color detector is disposed to detect indicator color changes of the liquid for providing indication back to the central computer for calculation of fluid presence, fluid equivalent points, and related fluid properties.

17 Claims, 1 Drawing Sheet

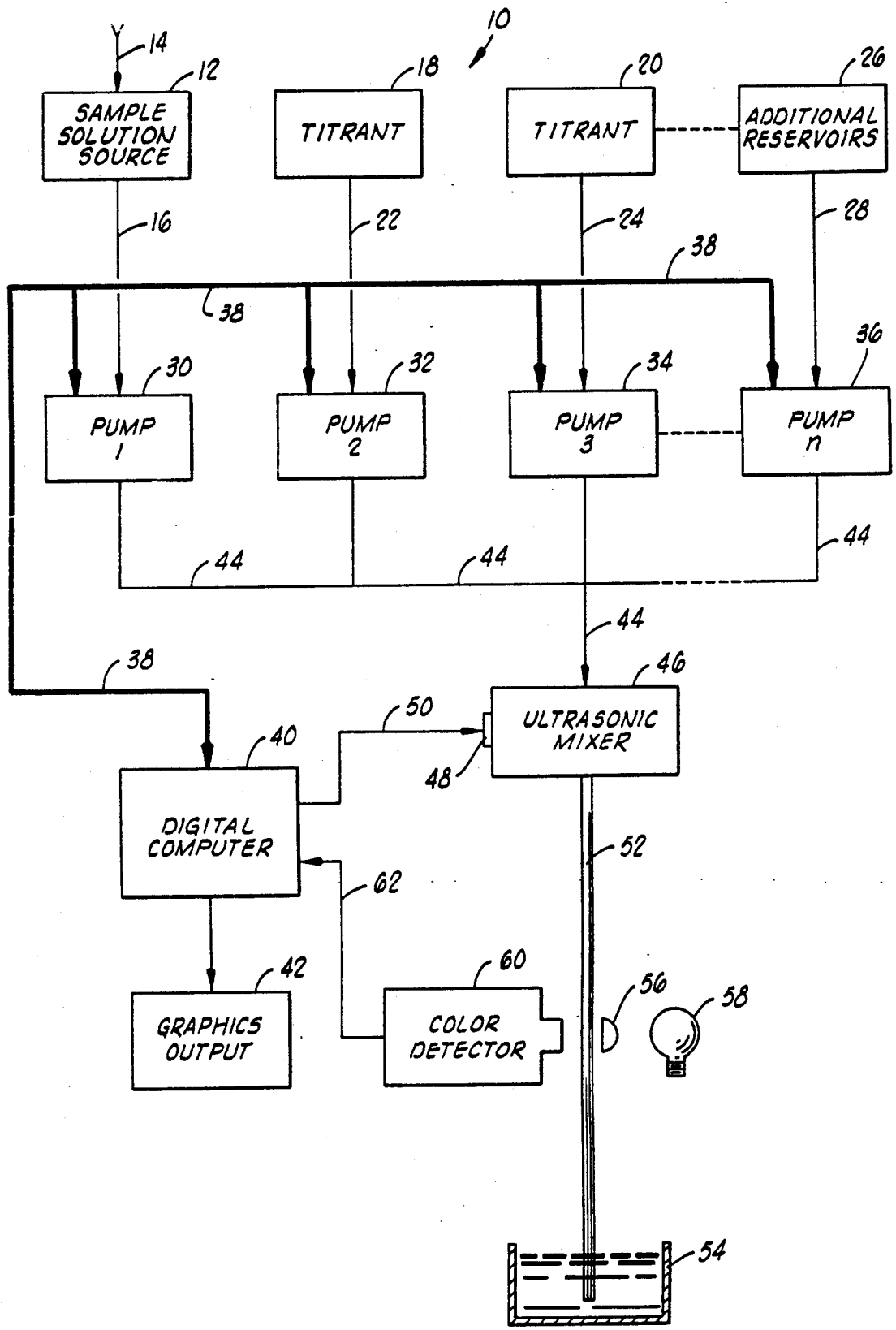

APPARATUS FOR AUTOMATIC TITRATION

BACKGROUND OF THE INVENTION

1. Field of the Invention

The invention relates generally to automatic titration devices and, more particularly, but not by way of limitation, it relates to an improved titration apparatus that can be used on-line with continuous selected liquids processing or in a batch processing mode.

2. Description of the Prior Art

The prior ar includes various types of titration device. At present, titration is generally performed by placing a solution in a container while another known chemical is slowly introduced to the solution. An operator can then monitor the mixing process to attempt to detect a color change in the mixture, such color change being indicative of an equivalence point in the mixture. The color change detection may be done visually or by a commercial type of color detector. U.S. Pat. No. 2,977,199 discloses a continuous testing device that may be employed with flowing liquids. In this device, a small portion of the flowing liquid is tapped off for introduction to a mixing chamber and subsequent flush to disposal. A controlled volume of titrant is introduced from a storage tank into the mixing chamber and a sensing device with indicator electrode, e.g. a platinum-rhenium alloy electrode, senses a potential change to provide an indication of the end point of the sample solution. The patent also discloses a situation where a colorimetric pH indicator is employed after mixing to provide a means for identifying the solution end-point.

U.S. Pat. No. 4,920,056 provides another teaching of an automated system for liquid-phase analysis. In this apparatus, a specified liquid sample and up to five reagents are delivered to a reaction cell by a stepper motor-driven syringe, and the contents of the cell are then mixed by spinning the cell. Sensing of the contents of the cell is done by a pH probe that derives an end point indication. The subject of the patent is to perform batch-mode liquid-phase reactions for chemical analysis on a microscale. The apparatus includes a reactor for receiving liquid from an automatic liquid sample injection valve and an automatic liquid reagent valve. A programmable electronic timer is then used to automatically control the injection and reagent valves in a programmed sequence and the analysis is completed by introducing the reaction mixture to a flow-through photometric detector to determine a reaction product of the sample and the reagent. Various types of sensor may be used to examine the reactor output.

Finally, another automatic titrator of the photometric type is taught in U.S. Pat. No. 3,073,682 wherein samples are delivered and tested in batch form. The device includes a titrating cell and means to feed a measured sample of main solution plus titrant thereto. Thereafter, a control circuit determines the end point of titration as well as a measure or indication of the volume of titrant added to effect neutralization of the particular sample. This device has desirable attributes of cleanliness and preservation of the purity of sample materials.

SUMMARY OF THE INVENTION

The present invention is an apparatus for quantitative analysis of certain titratable fluid combinations. A plurality of liquid sources or reservoirs containing solution sample, reagent, titrant and other liquids, are connected through respective ones of a plurality of rate-controlled pumps to a delivery tube which flows the liquid mixture into an ultrasonic mixer receiving high energy agitation. Subsequently, liquids are flowed into a mixing tube and a colorimetric detector is disposed to view liquid flow through the mixing tube to detect color change indications indicative of end point/equivalent point relationship. The detector delivers a signal indication to a control computer that is also programmed to provide pump rate control to the respective liquid pumps as well as to calculate chemical concentrations of the solution under test.

Therefore, it is an object of the present invention to provide an automatic titration system that is fast and accurate in making determinations.

It is also an object of the invention to provide a titration device that can test sample solutions from a pump manifold leading into a well casing to provide immediate determination of the fluid concentration.

It is yet another object of the present invention to provide a quantitative analysis device for checking well fluids that is fast, accurate and reliable in operation.

Finally, it is an object of the present invention to provide an on-line automatic titration device that assures complete and continuous mixing of sample, reagent and titrant liquid products.

Other objects and advantages of the invention will be evident from the following detailed description when read in conjunction with the accompanying drawing which illustrates the invention.

BRIEF DESCRIPTION OF THE DRAWING

The single drawing FIGURE is a block diagram of the automatic titrating device of the present invention.

DETAILED DESCRIPTION OF THE INVENTION

A titration device 10 includes a sample solution source 12, and this may be a reservoir and it may include an input 14 providing flow of sample liquid as it is extracted from an ancillary liquid process, e.g. wellhead work station or the like. Sample solution from source reservoir 12 is then available on a standardsize conduit 16. In like manner, a titrant reservoir 18 and a titrant reservoir 20 provide parallel flow through respective conduits 22 and 24. Additional reservoirs 26 for utilization in complex analysis schemes are connected to one or more conduits 28.

The sample conduit 16 is connected to the input of a pump 30 which is preferably a continuous flow type metering pump, a very accurate type of pump that is commercially available from Williams Company of Valencia, Calif. Conduit 22 is connected as input to a pump 32 and the titrant conduit 24 is connected into pump 34. The titrant reservoirs 18 and 20 and others so designated may contain reagents, indicators or mixtures thereof. Pumps 32 and 34 are preferably syringe-type pumps that operate under control of a stepping motor to provide very accurate pump throughput in smaller amounts. Such syringe pumps are commercially available from CAVRO Co. of Sunnyvale, Calif. Finally, any additional chemicals through conduit 28 may be introduced through a pump 36; that is, in the event that the particular analysis requires additional fluid input. Actually, some processes may require a plurality of additional chemicals whereupon a like plurality of pumps 36 will be employed to introduce fluids.

A control buss 38 is connected between a central control digital computer 40 and the respective pumps 30, 32, 34–36. Data buss 38 provides control signals to vary the pump rates at the various pumps as well as to provide continual pump rate data information to the digital computer 40. The computer 40 may be readily selected from any of a number of suitable microcomputers, and computer 40 is easily programmed to carry out the requisite fluid analysis calculations and flow rate controls. Graphics output 42 provides selected types of information readout relative to the analysis system.

Output from each of pumps 30, 32, 34–36 is input to a delivery tube 44, a uniform conduit providing fluid input to an ultrasonic mixer 46. The ultrasonic mixer 46 comprises a fluid container of optimum shape receiving energy irradiation between 17 and 40 kilohertz from a suitable transducer cartridge 48, and such mixer is commercially available from Vibra-Cell Company of Houston, Tex. Energization of the transducer 48 at a selected characteristic frequency may be generated in digital computer 40 as applied via line 50 or an independent energization source may be utilized. Output of the mixed fluids from mixer 46 is then applied through a transparent mixing tube 52 leading into a disposal reservoir 54.

The mixing tube 52 has a uniform but small inside diameter on the order of 0.03 to 0.06 inches. It is desirable that mixing tube 52 be constructed from non-wettable material. Processed fluid is passed by a transverse collimator lens 56 aligned with a light source 58 to direct a beam into a suitable color detector 60 which, in turn, generates pulse output responsive to color changes detected within mixing tube 52. Pulse output from color detector 60 is via line 62 for input to digital computer 40. One suitable form of color detector is commercially available from Datalogic Optic Electronics, Inc. of Cary, N.C.

The automatic titration system 10 is capable of operation in a selected one of two modes, a batch processing mode and a continuous mode. The batch processing mode enables the sampling of a multiple of fluids which may then be subject to reaction to identify the types of fluids. For example, these may be the various fluids contained within naturally occurring well bore fluids. Thus, an operator may travel with portable titration equipment to a field location whereupon the operator can draw a fluid sample from a well bore or tank at the drilling site and place the sample solution in the source reservoir 12 subject to flow by pump 30. An additional plurality of pumps 32, 34–36, e.g. five pumps, might then be associated with respective reservoirs 18, 20–26 that contain selected standard reagents.

Titration under control of digital computer 40 may then examine successive portions of sample solution from source reservoir 12 with respective reagents to identify, for example, phosphors, barium, calcium, chlorides, etc. Suitable program control of digital computer 40 will enable such sequential fluid sample examination as the sample with successive reagents is flowed through delivery tube 44 and the ultrasonic mixer 46 to the mixing tube 52 whereupon color detector 60 provides indication output to the digital computer 40. In some cases where an indicator chemical is required in combination with the particular reagent, the indicator can be added directly into the solution in the reservoirs 18, 20–26. Standard indicators for use at all pH ranges may be used, e.g. the Indicat AR series.

When operating in the continuous mode, the sample solution may be a well additive. That is, the input 14 may be directing fluid from the low pressure side of a pump that is moving the fluid downhole. A reservoir 18 may be filled with a suitable indicator and reservoir 20 may include a suitable titrant such that the flow of pumps 30, 32 and 34 as controlled by digital computer 40 would place a continuous volume of sample solution from pump 30 onto delivery tube 44 as a much lesser flow of indicator is applied via pump 32 along with a syringe-regulated flow of titrant through pump 34. For example, this may be an aqueous solution of hydrochloric acid well additive with phenolphthalein indicator and sodium hydroxide titrant. Then when the amount of titrant exceeds the equivalent point the pH change causes color change in mixing tube 52 which is detected by the color detector 60. This will probably not be fast acting enough such that the digital computer 40 will again increase sample input to bring the overmixture back more exactly to the equivalent point. By rocking or hunting the mixture about the equivalent point, i.e., above and below equivalents, computer 40 is able to generate a more exact digital output value for the graphics presentation.

Whether used in the batch process mode or continuous mode, the system has the advantage of using the single delivery tube with ultrasonic mixer providing very rapid and thorough agitation and mixture of the solution materials as it is delivered into mixer tube 52 for inspection by the color detector or similar sensor.

The digital computer 40 functions to direct sequencing and pump speed rate for each of the pumps 30, 32, 34 and 36. The computer 40 also receives input of an on-off pulse voltage from detector 60 at very fast speeds to enable close determination about the equivalent point. The digital computer 40 also is programmed to make calculations from the pump speeds and concentration of titrant to determine quantitative aspects of the fluid sample being tested.

Changes may be made in combination and arrangement of elements as heretofore set forth in the specification and shown in the drawing; it being understood that changes may be made in the embodiments disclosed without departing from the spirit and scope of the invention as defined in the following claims.

What is claimed is:

1. Apparatus for continuous titration of liquid sample comprising:
   a delivery tube;
   first means including a sample source for receiving and pumping a continuous flow of liquid sample into said delivery tube;
   second means including a reservoir for pumping reagent at a controlled rate into said delivery tube;
   third means including a reservoir for pumping selected titrant at a controlled rate into said delivery tube;
   an ultrasonic mixer receiving liquids from said delivery tube;
   a mixing tube passing mixed liquids from said ultrasonic mixer therethrough;
   optical detector means disposed in viewing relationship adjacent to said mixing tube and producing an output signal indicative of sample titrant fluid equivalence; and
   a computer receiving said detector means output signal and producing a first signal output to control the first means for receiving and pumping liquid sample, a second signal output to control the second means for pumping reagent, and a third signal output to control the third means for pumping titrant.

2. Apparatus as set forth in claim 1 wherein said second means for pumping reagent comprises:
a metering pump moving the reagent to the delivery tube at a rate controlled by the second signal output from the computer.

3. Apparatus as set forth in claim 1 wherein said third means for pumping titrant comprises:
a metering pump moving the titrant to the delivery tube at a rate controlled by the third signal output from the computer.

4. Apparatus as set forth in claim 2 wherein said third means for pumping titrant comprises:
a metering pump moving the titrant to the delivery tube at a rate controlled by the third signal output from the computer.

5. Apparatus as set forth in claim 4 wherein:
said metering pumps are syringe-type pumps.

6. Apparatus as set forth in claim 1 wherein said ultrasonic mixer comprises:
a mixing enclosure receiving liquid input from said delivery tube; and
means irradiating the mixing enclosure with ultrasonic energy in the range of 17 to 40 kilohertz.

7. Apparatus as set forth in claim 4 wherein said ultrasonic mixer comprises:
a mixing enclosure receiving liquid input from said delivery tube; and
means irradiating the mixing enclosure with ultrasonic energy in the range of 17 to 40 kilohertz.

8. Apparatus as set forth in claim 1 wherein said optical detector means comprises:
a color detector disposed in optically viewing relationship to said mixing tube.

9. Apparatus as set forth in claim 4 wherein said optical detector means comprises:
a color detector disposed in optically viewing relationship to said mixing tube.

10. Apparatus as set forth in clam 6 wherein said optical detector means comprises:
a color detector disposed in optically viewing relationship to said mixing tube.

11. An automatic titration device for identifying type and concentration of a liquid sample, comprising:
a first source of liquid sample;
a delivery tube for receiving said liquid sample at a first rate of flow;
plural means for storing and introducing a titrant and a selected reagent into said delivery tube at a second rate of flow;
an ultrasonic energy mixer receiving flow from said delivery tube and outputting flow of mixed liquid consisting of sample, titrant and reagent into a mixing tube;
a computer providing a control buss output connected to said first source of liquid sample and said plural means for storing and introducing to control said first rate of flow and said second rate of flow; and
a color detector adjacent to said mixing tube for optically viewing the mixing tube and sensing the color change occurring when the liquid sample and titrant with reagent react, said color detector producing an indicator signal for input to said computer.

12. A device as set forth in claim 11 wherein said plural means for storing and introducing a titrant and a reagent comprises:
a second source of titrant connected for flow to said delivery tube at a controlled rate; and
a third source of reagent connected for flow to said delivery tube at a controlled rate.

13. A device as set forth in claim 11 wherein said ultrasonic energy mixer comprises:
an elongated chamber receiving input flow from said delivery tube; and
a transducer directed to irradiate flow from the delivery tube within said elongated chamber with ultrasonic energy in the 17 to 40 kilohertz range.

14. A device as set forth in claim 12 wherein said ultrasonic energy mixer comprises:
an elongated chamber receiving input flow from said delivery tube; and
a transducer directed to irradiate flow from the delivery tube within said elongated chamber with ultrasonic energy in the 17 to 40 kilohertz range.

15. A device as set forth in claim 11 which is further characterized to include:
a plurality of reservoirs connected for flow to said delivery tube at a controlled rate for the selected addition of titrant and reagent.

16. A device as set forth in claim 11 which is further characterized to include:
a first pump of continuous flow type which is connected to the first source of liquid sample and which moves liquid sample into said delivery tube.

17. A device as set forth in claim 16 wherein said plural means for storing and introducing a titrant and a selected reagent comprises:
a second source of titrant;
a second pump of metering type for introducing said titrant into said delivery tube;
a third source of reagent; and
a third pump of metering type for introducing said reagent into said delivery tube.

* * * * *